United States Patent
Gnep et al.

(10) Patent No.: US 7,872,166 B2
(45) Date of Patent: Jan. 18, 2011

(54) PROCESS FOR ISOMERIZING AROMATIC C8 COMPOUNDS IN THE PRESENCE OF A CATALYST COMPRISING A MODIFIED EUO ZEOLITE

(75) Inventors: Ngi Suor Gnep, Bignoux (FR); Emmanuelle Guillon, Vernaison (FR); Sylvie Lacombe, Vernaison (FR); Laurent Simon, Villeurbanne (FR); Pierre Moreau, Ussel (FR); Patrick Magnoux, Poitiers (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 389 days.

(21) Appl. No.: 11/955,825

(22) Filed: Dec. 13, 2007

(65) Prior Publication Data

US 2008/0221376 A1    Sep. 11, 2008

(30) Foreign Application Priority Data

Dec. 13, 2006 (FR) .................................. 06 10979

(51) Int. Cl.
*C07C 5/27* (2006.01)
(52) U.S. Cl. ........................ 585/480; 585/481; 585/482
(58) Field of Classification Search ................. 585/480, 585/481, 482
See application file for complete search history.

(56) References Cited

U.S. PATENT DOCUMENTS

| | | | |
|---|---|---|---|
| 4,593,138 A * | 6/1986 | Casci et al. ................. | 585/481 |
| 4,695,667 A | 9/1987 | Sumitani et al. | |
| 5,516,736 A * | 5/1996 | Chang et al. .................. | 502/64 |
| 6,051,519 A | 4/2000 | Wu et al. | |
| 6,057,486 A | 5/2000 | Merlen et al. | |
| 6,660,896 B1 | 12/2003 | Buchanan et al. | |
| 2005/0000859 A1 | 1/2005 | Hung et al. | |

* cited by examiner

*Primary Examiner*—Thuan Dinh Dang
(74) *Attorney, Agent, or Firm*—Millen, White, Zelano & Branigan, P.C.

(57) ABSTRACT

A process for isomerizing a feed comprising at least one aromatic compound containing eight carbon atoms per molecule is carried out in the presence of a catalyst comprising at least one modified zeolite with structure type EUO, at least one binder and at least one metal from group VIII of the periodic table, said catalyst having been prepared using a process which comprises the following in succession:

a) a step for treatment of a zeolite with structure type EUO in the presence of at least one molecular compound containing at least one silicon atom, during which said compound, with a diameter greater than the maximum pore opening diameter in said zeolite, is deposited in the gas phase on the outer surface of said zeolite;

b) at least one heat treatment step;

c) forming said zeolite with a binder;

d) at least one step for introducing at least one metal from group VIII of the periodic table onto a support based on said modified and formed zeolite.

17 Claims, No Drawings

PROCESS FOR ISOMERIZING AROMATIC C8 COMPOUNDS IN THE PRESENCE OF A CATALYST COMPRISING A MODIFIED EUO ZEOLITE

The present invention relates to isomerizing an aromatic feed comprising at least one aromatic compound containing eight carbon atoms. Said feed intended for use in the present invention is a feed containing ethylbenzene, a mixture of xylenes or a mixture of xylene and ethylbenzene. This feed is usually termed an "aromatic c8 cut".

More particularly, the present invention relates to a process for isomerizing an aromatic feed comprising at least one aromatic compound containing eight carbon atoms per molecule which is aimed at maximizing the production of para-xylene.

PRIOR ART

Catalysis of the isomerization of ethylbenzene into xylenes necessitates the presence of a group VIII metal. Optimized formulations based on mordenite and a group VIII metal produce catalysts on which side reactions are still non-negligible. An example which may be cited is the opening of naphthene rings, which may or may not be followed by cracking or disproportionation and transalkylation of C8 aromatics, which results in the formation of unwanted aromatic compounds. Thus, it is of particular interest to discover novel, more selective catalysts.

Zeolites used for isomerizing a c8 aromatic cut include ZSM-5 used alone or mixed with other zeolites, such as mordenite. Said catalysts have been described in U.S. Pat. No. 4,467,129, U.S. Pat. No. 4,482,773 and EP-B 0 013 617. Other catalysts principally based on mordenite have been described, for example, in French patent application FR-A-2 477 903 and in patents U.S. Pat. No. 4,723,051 and U.S. Pat. No. 4,665,258. The lack of selectivity of mordenite may be attenuated by optimizing formulations and/or by specific dealumination treatments as has, for example, been described in the Applicant's FR-B-2 691 914. These techniques can reduce unwanted disproportionation reactions.

More recently, a catalyst based on a zeolite with structure type EUO (EP-A1-0 928 987) has been proposed. International patent application WO-A-2005/065380 describes the use of a zeolite with structure type MTW for the isomerization of xylenes and ethylbenzene.

Further, a number of patents have already dealt with methods for modifying zeolites to improve the activity or selectivity of catalysts for different catalytic processes. In particular, U.S. Pat. No. 4,402,867 describes a method for preparing a catalyst based on zeolite comprising a step consisting of depositing, in the aqueous phase, at least 0.3% by weight of amorphous silica in the pores of the zeolite. U.S. Pat. No. 4,996,034 describes a process for substituting aluminium atoms present in a zeolitic framework with silicon atoms, said process being carried out in one step in an aqueous medium using fluorosilicate salts. U.S. Pat. No. 4,451,572 describes the preparation of a zeolitic catalyst comprising a step for depositing organosilicon substances in the vapour or liquid phase, the target zeolites being wide pore zeolites, in particular Y zeolite.

SUMMARY AND ADVANTAGE OF THE INVENTION

The present invention concerns a process for isomerizing a feed comprising at least one aromatic compound containing eight carbon atoms per molecule carried out in the presence of at least one catalyst comprising at least one modified zeolite with structure type EUO, at least one binder and at least one metal from group VIII of the periodic table, said catalyst having been prepared using a process which comprises at least the following in succession:

a) a step for treatment of a zeolite with structure type EUO in the presence of at least one molecular compound containing at least one silicon atom, during which said compound, with a diameter greater than the maximum pore opening diameter in said zeolite, is deposited in the gas phase on the outer surface of said zeolite;

b) at least one heat treatment step;

c) forming said zeolite with a binder;

d) at least one step for introducing at least one metal from group VIII of the periodic table onto a support based on said modified and formed zeolite.

Said catalyst used to carry out the isomerization process of the invention is in the form of extrudates or beads. It advantageously comprises at least one additional metal selected from the group formed by elements from groups IIIA, IVA and VIIB of the periodic table.

It has surprisingly been discovered that a catalyst in the form of extrudates or beads comprising at least one zeolite with structure type EUO and modified so that a layer of amorphous silica is deposited on the outer surface of the crystals of said zeolite, at least one binder and at least one metal from group VIII of the periodic table results in improved catalytic performances as regards activity when it is used in a process for isomerization of a feed comprising at least one aromatic compound containing eight carbon atoms per molecule. In particular, such a catalyst is more active than a catalyst based on a zeolite with structure type EUO modified by a treatment step carried out in the liquid phase in the presence of at least one molecular compound comprising at least one silicon atom. It is also particularly selective as regards the desired products, namely xylenes and in particular para-xylene. It is particularly advantageous to have available a catalyst which is both active and selective, which can increase the yield of the desired product. A layer of silica deposited on the outer surface using a gas phase treatment can produce high activity and high selectivity.

DESCRIPTION OF THE INVENTION

The present invention pertains to a process for isomerizing a feed comprising at least one aromatic compound containing eight carbon atoms per molecule carried out in the presence of at least one catalyst comprising at least one modified zeolite with structure type EUO, at least one binder and at least one metal from group VIII of the periodic table, said catalyst having been prepared using a process which comprises at least the following in succession:

a) a step for treatment of a zeolite with structure type EUO in the presence of at least one molecular compound containing at least one silicon atom, during which said compound, with a diameter greater than the maximum pore opening diameter in said zeolite, is deposited in the gas phase on the outer surface of said zeolite;

b) at least one heat treatment step;

c) forming said zeolite with a binder;

d) at least one step for introducing at least one metal from group VIII of the periodic table onto a support based on said modified and formed zeolite.

In accordance with the invention, said catalyst used to carry out the isomerization process of the invention comprises at least one group VIII metal selected from iron, cobalt, nickel, ruthenium, rhodium, palladium, osmium, iridium and platinum, preferably selected from noble metals, more preferably selected from palladium and platinum and still more preferably platinum. The dispersion of the group VIII metal(s), determined by chemisorption, for example by $H_2$—$O_2$ titration or by chemisorption of carbon monoxide, is in the range 50% to 100%, preferably in the range 60% to 100% and more preferably in the range 70% to 100%. The macroscopic distribution coefficient of the group VIII metal(s), obtained from its profile determined by Castaing microprobe, defined as the ratio of the concentrations of the group VIII metal(s) at the grain core with respect to the edge of that grain, is in the range 0.7 to 1.3, preferably in the range 0.8 to 1.2. The value of this ratio, close to 1, is evidence of the homogeneity of the distribution of the group VIII metal(s) in the catalyst.

Said catalyst advantageously comprises at least one additional metal selected from the group formed by elements from groups IIIA, IVA and VIIB of the periodic table, preferably selected from gallium, indium, tin and rhenium. Said additional metal is preferably selected from indium, tin and rhenium.

Said catalyst also advantageously includes sulphur.

More particularly, said catalyst used to carry out the isomerization process of the invention contains:
- 1% to 90%, preferably 3% to 80% and more preferably 4% to 60% by weight, of said modified zeolite with structure type EUO;
- 0.01% to 4%, preferably 0.05% to 2.0% by weight, of at least one metal from group VIII of the periodic table;
- optionally, 0.01% to 2%, preferably 0.05% to 1% by weight of at least one additional metal selected from the group formed by elements from groups IIIA, IVA and VIIB;
- optionally, a sulphur content such that the ratio of the number of atoms of sulphur to the number of atoms of metal(s) from group VIII is in the range 0.3:1 to 2:1;
- at least one binder providing the complement to 100% in the catalyst.

Said catalyst is in the form of beads or extrudates, preferably in the form of extrudates.

In accordance with the invention, the initial zeolite with structure type EUO which has not yet been modified for inclusion in the catalyst used to carry out the isomerization process of the invention has a microporous one-dimensional framework with a pore diameter of 4.1×5.4 Å (1 Å=1 Angstrom=$10^{-10}$ m) ("Atlas of zeolite framework types", Ch Baerlocher, W M Meier and D H Olson, $5^{th}$ edition, 2001). Further, N A Briscoe et al have disclosed, in an article in the review Zeolites (1988, 8, 74), that these one-dimensional channels have side pockets with a depth of 8.1 Å and a diameter of 6.8×5.8 Å. Said zeolite with structure type EUO is selected from EU-1, ZSM-50 and TPZ-3 zeolites; it is preferably EU-1.

The synthesis of EU-1 zeolite and its physico-chemical characteristics have already been described in EP-B1-0 042 226. U.S. Pat. No. 4,640,829 describes ZSM-50 zeolite and its preparation process. TPZ-3 zeolite and its preparation process are disclosed in EP-A1-0 051 318.

Zeolite with structure type EUO, modified using the various steps of the process for preparing the catalyst used to carry out the isomerization process of the invention, initially contains, i.e. before being modified in step a), at least silicon and at least one element T selected from the group formed by aluminium, iron, gallium and boron, preferably aluminium and boron and more preferably aluminium, in a proportion such that the atomic ratio Si/T, preferably the atomic ratio Si/Al, is preferably in the range 2:1 to 100:1, more preferably in the range 5:1 to 80:1 and still more preferably in the range 5:1 to 50:1. Said zeolite with structure type EUO, preferably said EU-1 zeolite, used to carry out said step a) of the process for preparing the catalyst used to carry out the isomerization process of the invention, is in the calcined form and contains at least one proton so that it is in the protonated form (hydrogen form $H^+$), in which the amount of cation other than $H^+$ is less than 30% of the total number of cations, preferably less than 20% and more preferably less than 15% with respect to the total number of cations on the zeolite. In the case in which, prior to carrying out said step a) of the catalyst preparation process, the zeolite to be modified is in the as synthesized from, still containing the organic template used to prepare it, said zeolite may be calcined at a temperature in the range 300° C. to 700° C., preferably in the range 400° C. to 600° C., then if the zeolite contains one or more alkali/alkaline-earth metal(s), one or more ion exchange steps may be carried out using a solution containing at least one ammonium salt, for example ammonium nitrate $NH_4NO_3$, to eliminate at least part, preferably almost all of the alkali cation present in the zeolite. A step for calcining in a stream of dry air at a temperature generally in the range about 400° C. to 500° C. is intended to generate the formation of protons in the zeolite by desorption of ammonia, thereby producing the hydrogen form of the zeolite, which is ready for carrying out said step a) of the process for preparing the catalyst used to carry out the isomerization process of the invention.

Said zeolite with structure type EUO, preferably EU-1 zeolite, used to carry out said step a) of the catalyst preparation process, is an acidic zeolite containing between 70% and 100%, preferably between 80% and 100% and more preferably between 85% and 100% of compensating cations in the protonic form $H^+$, the remainder of the cations preferably being selected from metals from groups IA and IIA of the periodic table; more particularly, said cation(s) is (are) selected from the cations $Na^+$, $Li^+$, $K^+$, $Rb^+$, $Cs^+$, $Ba^{2+}$ and $Ca^{2+}$. In particular, the sodium content is preferably such that the atomic ratio Na/T, preferably the ratio Na/Al, is less than 0.5:1, preferably less than 0.1:1, and more preferably less than 0.02:1.

The zeolite with structure type EUO, for example EU-1 zeolite, which is in the composition of the catalyst used to carry out the isomerization process of the invention, generally has a specific surface area, measured by chemisorption of nitrogen using the BET method, of more than 300 $m^2$/g. Preferably, its specific surface area is more than 400 $m^2$/g.

The catalyst used to carry out the isomerization process of the invention is prepared using a process comprising, in a first step, at least one step a) consisting of selectivisation of said zeolite with structure type EUO, preferably EU-1 zeolite. The term "selectivisation" as used in the present invention means neutralizing the acidity of the outer surface of each of the zeolite crystals. The acidity may be neutralized using any method which is known to the skilled person. Conventional methods to carry out specific selectivisation of acid sites on the outer surface of a zeolite generally employ molecules with a kinetic diameter which is greater than the pore opening diameter of the zeolite. More precisely, said selectivisation step a) consists of treating said zeolite with structure type EUO, in its protonated form, in the presence of at least one molecular compound containing at least one silicon atom the diameter of which is greater than the maximum opening diameter of the pores in the zeolite with structure type EUO, preferably EU-1 zeolite, to be treated in step a). Preferably, the catalyst preparation process comprises a single step a).

The molecules generally used to passivate or selectivise the outer surface of the zeolite with structure type EUO, preferably EU-1 zeolite, are compounds containing atoms which may interact with the outer surface sites of each of the zeolite crystals. The molecules used in accordance with the invention are organic or inorganic molecules containing one or more atom(s) of silicon. Accordingly, in said step a) of the process for preparing the catalyst used to carry out the isomerization process of the invention, the protonated zeolite undergoes a step for treatment in the presence of at least one molecular compound containing at least one silicon atom. Said step a) allows a layer of said molecular compound containing at least one silicon atom to be deposited on the outer surface of said zeolite with structure type EUO which, after step b) is transformed into a layer of amorphous silica on the outer surface of each of the zeolite crystals. Preferably, the molecular compound containing at least one silicon atom is selected from compounds with formula Si—$R_4$ and $Si_2$—$R_6$ where R may be either hydrogen or an alkyl, aryl or acyl group, or an alkoxy group (O—R'), or a hydroxyl group (—OH) or a halogen, preferably an alkoxy group (O—R'). In one and the same molecule Si—$R_4$ and $Si_2$—$R_6$, group R may be either identical or different. As an example, molecular compounds with formula $Si_2H_6$ or $Si(C_2H_5)_3(CH_3)$ may fit the above formulae. Thus, the molecular compound containing at least one silicon atom used in step a) of the process for preparing the catalyst used to carry out the isomerization process of the invention may be a silane, disilane, alkylsilane, alkoxysilane or siloxane type compound. Highly preferably, said molecular compound has a composition with general formula Si—$(OR')_4$ where R' is an alkyl, aryl or acyl group, preferably an alkyl group and more preferably an ethyl group. Said molecular compound used to carry out said step a) has a diameter which is greater than the maximum pore opening diameter of the zeolite with structure type EUO, preferably EU-1 zeolite, and preferably comprises at most two silicon atoms per molecule. The molecular compound tetraethylorthosilicate (TEOS) with formula $Si(OCH_2CH_3)_4$, which has a diameter of 9.6 Å, is highly advantageous for carrying out said step a) of the process for preparing the catalyst used to carry out the isomerization process of the invention.

Said step a) of the process for preparing the catalyst used to carry out the isomerization process of the invention, which consists of treating protonated zeolite in the presence of at least one molecular compound containing at least one silicon atom, is carried out by depositing said compound on the outer surface of the zeolite. In accordance with the invention, said step a) is carried out by depositing said molecular compound containing at least one silicon atom in the gas phase.

Step a) for preparing the catalyst used to carry out the isomerization process of the invention is carried out in a fixed bed reactor. Prior to the gas phase deposition reaction (CVD) in said fixed bed reactor, the zeolite with structure type EUO, preferably EU-1 zeolite, is preferably activated. Activation of said zeolite in the fixed bed reactor is carried out in oxygen, in air or in inert gas, or in a mixture of air and inert gas or oxygen and inert gas. The activation temperature of the zeolite is advantageously in the range 100° C. to 600° C., and highly advantageously between 300° C. and 550° C. The molecular compound containing at least one silicon atom which has to be deposited on the outer surface of each of the crystals of zeolite is sent to the vapour phase reactor, said molecular compound being diluted in a vector gas which may be either hydrogen ($H_2$), or air, or argon (Ar) or helium (He) or nitrogen ($N_2$); preferably the vector gas is an inert gas selected from Ar, He and $N_2$. Said molecular compound containing at least one silicon atom is deposited on the outer surface of said zeolite in the vapour phase, in the absence of any hydrocarbon compound. To obtain a layer of amorphous silica of optimum quality on the outer surface of the zeolite with structure type EUO, it is necessary to select the operating conditions for depositing the molecular compound containing at least one silicon atom carefully. In particular, the temperature of the zeolite bed during deposition is preferably in the range 10° C. to 300° C., and more preferably in the range 50° C. to 200° C., the partial pressure, in the gas phase, of the molecular compound to be deposited on the outer surface of the zeolite is preferably in the range 0.001 to 0.5 bars, more preferably in the range 0.01 to 0.2 bars; the deposition duration is preferably in the range 10 minutes to 10 hours and more preferably in the range 30 minutes to 5 hours, and still more preferably in the range 1 to 3 hours.

In accordance with step b) of the process for preparing the catalyst used to carry out the isomerization process of the invention, the molecular compound containing at least one silicon atom is decomposed by a heat treatment which is carried out at a temperature which is preferably in the range 200° C. to 700° C., more preferably in the range 300° C. to 500° C. Said heat treatment step is carried out in air, in oxygen, in hydrogen, in nitrogen or in argon or in a mixture of nitrogen and argon. The duration of this treatment is advantageously in the range 1 to 5 hours. At the end of said heat treatment, a layer of amorphous silica is deposited on the outer surface of each of the crystals or zeolite with structure type EUO. In accordance with the invention, the inner surface of each of the crystals of zeolite with structure type EUO is preferably free of a deposit of an amorphous layer of silica. The maximum pore opening diameter of the modified zeolite present in the catalyst used to carry out the isomerization process of the invention is preferably unchanged with respect to that of the initial non-modified zeolite.

In accordance with step c) of the process for preparing the catalyst used to carry out the isomerization process of the invention, the zeolite with structure type EUO from said step b) is mixed with at least one binder then formed. The catalyst is generally formed so that the catalyst is in the form of extrudates or beads, preferably in the form of extrudates. The conditions for forming the modified zeolite with structure type EUO, the choice of binder, optional milling of said zeolite, the peptization process, addition of pore-forming agents, the mixing time, the extrusion pressure if the catalyst is shaped into extrudates, and the drying rate and time are determined for each binder in accordance with rules which are well known to the skilled person so as to obtain a catalyst in the form of beads of extrudates, preferably in the form of extrudates.

The binder is a porous amorphous or poorly crystalline oxide type mineral element. It is selected from the group formed by clays, magnesia, aluminas, silicas, titanium oxide, boron oxide, zirconia, aluminium phosphates, titanium phosphates, zirconium phosphates and silica-aluminas. Charcoal may also be used. Preferably, the binder is alumina.

Forming advantageously consists of mixing the modified zeolite with structure type EUO, for example modified EU-1 zeolite, in a moist gel of binder (generally obtained by mixing at least one acid and a binder powder), preferably alumina, for a period necessary to obtain good homogeneity of the paste, for example for about ten minutes, then passing the paste obtained through a die to form extrudates, for example with a diameter of 0.4 to 4 mm. Forming is generally followed by drying, for example for several hours at about 120° C. in an oven, and calcining, generally at a temperature of 250° C. to 600° C., for example for two hours at about 400° C. Said modified and formed zeolite with structure type EUO constitutes the support of the catalyst used to carry out the isomerization process of the invention.

In step d) of the process for preparing the catalyst used to carry out the isomerization process of the invention, at least one group VIII metal is introduced onto the support based on said formed zeolite with modified structure type EUO. Depending on the method used to introduce said group VIII metal, as will be indicated below, said group VIII metal, preferably platinum, is deposited mainly either on the modified zeolite or on the binder. The metal(s) from group VIII of the periodic table and optional additional metal(s) is (are) introduced either all in the same manner or using different techniques. Preferably, at least said metal from group VIII of the periodic table is introduced by selective deposition on the support based on said modified zeolite and formed with the binder using any process which is known to the skilled person. Said deposition is, for example, carried out by dry impregnation, excess impregnation or by ion exchange. Advantageously, deposition is carried out so that the dispersion of said group VIII metal or metals, determined by chemisorption, is in the range 50% to 100%, preferably in the range 60% to 100% and more preferably in the range 70% to 100% and such that the coefficient of macroscopic distribution of said group VIII metal or metals, defined as the ratio of the concentrations of each group VIII metal in the core of the grain with respect to the edge of that grain, is in the range 0.7:1 to 1.3:1, preferably in the range 0.8:1 to 1.2:1.

To introduce the various metals into the composition of the catalyst, any precursors of said metals are suitable for deposition of said elements.

The platinum, preferably selected as the group VIII metal, is generally introduced into the modified structure type zeolite and/or onto the binder. For any noble metal from group VIII, ammoniacal compounds or compounds such as ammonium chloroplatinate, dicarbonyl platinum dichloride, hexahydroxyplatinic acid, palladium chloride or palladium nitrate may be used.

Controlling certain parameters during deposition of said group VIII metal(s), in particular the nature of the precursor of said group VIII metal(s) used, allows the deposition of said metal(s) to be orientated mainly towards the binder or towards the zeolite.

Introducing the group VIII metal(s), in particular platinum, using ammoniacal precursors, mainly results in deposition of said metal, in particular platinum, on the modified zeolite with structure type EUO. Said ammoniacal precursors for preparing the catalyst are introduced by cation exchange. In particular, when said group VIII metal is platinum, the precursor is advantageously selected from ammoniacal compounds such as platinum (II) tetramine salts with formula $Pt(NH_3)_4X_2$, platinum (IV) hexamine salts with formula $Pt(NH_3)_6X_4$; platinum (IV) halogenopentammine salts with formula $(PtX(NH_3)_5)X_3$ and platinum N-tetrahalogenodiamine salts with formula $PtX_4(NH_3)_2$. Halogenated compounds with formula $H(Pt(acac)_2X)$, X being a halogen selected from the group formed by chlorine, fluorine, bromine and iodine, X preferably being chlorine, and "acac" representing the acetylacetone group (with empirical formula $C_5H_7O_2$), derived from acetyl acetone, are also advantageously selected as the platinum precursor so that the platinum is mainly deposited on the modified zeolite with structure type EUO by cation exchange.

Introducing the group VIII metal(s) by anion exchange mainly results in the deposition of said metal(s) on the binder. In particular, to introduce platinum or palladium, anion exchange with hexachloroplatinic acid and/or hexachloropalladic acid may be carried out in the presence of a competing agent, for example hydrochloric acid, deposition generally being carried out by calcining, for example for about 2 hours at about 400° C.

Introduction of at least one additional metal selected from the group formed by elements from groups IIIA, IVA and VIIB of the periodic table in the catalyst during said step d) for preparing said catalyst may be carried out using any suitable deposition technique known to the skilled person and any suitable precursor for said additional metals. In particular, the group VIII metal(s) and the additional metal(s) selected from metals from groups IIIA, IVA and VIIB are added separately or simultaneously during said step d). The additional metal(s) may be introduced using precursors such as chlorides, bromides or nitrates of elements from groups IIIA, IVA and VIIB. As an example in the case of indium, the nitrate or chloride is advantageously used, and in the case of rhenium, perrhenic acid is used. The additional metal(s) may also advantageously be introduced in the form of at least one organic compound selected from the group constituted by complexes of said metal(s), in particular polyketone complexes of the metal and hydrocarbylmetals such as metal alkyls, cycloalkyls, aryls, alkylaryls and arylalkyls. In this latter case, said additional metal is advantageously introduced using a solution of an organometallic compound of said metal in an organic solvent. It is also possible to use as organohalogen compounds of said metal a precursor for said additional metal(s). It is also advantageous to use, as a precursor for said additional metal(s), organic compounds of said additional metal(s), in particular tetrabutyltin in the case of tin, and triphenylindium in the case of indium.

If the additional metal is introduced before the group VIII metal(s), the precursor for said additional metal used is generally selected from the group constituted by the halide, nitrate, acetate, tartrate, carbonate and oxalate of said additional metal. Introduction is advantageously carried out in aqueous solution. It may also be advantageous to introduce said additional metal(s) using a solution of an organometallic compound of said metal(s), for example tetrabutyltin. In this case, before introducing at least one group VIII metal, calcining is carried out in air.

The group VIII metal(s), preferably noble metals from the platinum family, and optionally the additional metal, are preferably introduced by impregnation using an aqueous or organic solution of one of the organometallic compounds cited above. Organic solvents which may be used which may be cited include paraffinic, naphthenic or aromatic hydrocarbons containing, for example, 6 to 12 carbon atoms per molecule, and halogenated organic compounds containing 1 to 12 carbon atoms per molecule, for example. Examples which may be cited are n-heptane, methylcyclohexane, toluene and chloroform. It is also possible to use mixtures of solvents.

Further, intermediate treatments such as calcining and/or reduction may be applied between the successive depositions of the various metals.

Preparation of the catalyst used to carry out the isomerization process of the invention is generally terminated by calcining, normally at a temperature of about 250° C. to 600° C., for a period of about 0.5 to 10 hours, preferably preceded by drying, for example oven drying, at a temperature from ambient temperature to 250° C., preferably 40° C. to 200° C. Said drying step is preferably carried out during the temperature ramp-up necessary to carry out said calcining.

It is advantageous to carry out prior reduction of the catalyst ex situ, in a stream of hydrogen, for example at a temperature of 450° C. to 600° C., for a period of 0.5 to 4 hours. In the case in which the catalyst used to carry out the isomerization process of the invention contains no sulphur, reduction in hydrogen of the metal(s) present in the composition of the catalyst is carried out in situ before injecting the feed.

The catalyst used to carry out the isomerization process of the invention is prepared in accordance with steps a) to d) described above before its introduction into the reactor carrying out the isomerization reaction: the catalyst is brought into contact with said feed comprising at least one aromatic compound containing eight carbon atoms when at least preparation steps a) to d) described above have been carried out.

When the catalyst used to carry out the isomerization process of the invention contains sulphur, the sulphur is introduced onto the formed and calcined catalyst containing the metal or metals cited above, either in situ before the catalytic reaction or ex situ. Any sulphurization is carried out after reducing the catalyst. In the case of in situ sulphurization, if the catalyst has not already been reduced, reduction is carried out before sulphurization. In the case of ex situ sulphurization, reduction is carried out followed by sulphurization. Sulphurization is carried out in the presence of hydrogen using any sulphurization agent which is well known to the skilled person, such as dimethyldisulphide or hydrogen sulphide. As an example, the catalyst may be treated with a feed containing dimethyldisulphide in the presence of hydrogen, with a concentration such that the (sulphur/group VIII metal(s)) ratio is in the range 0.3:1 to 2:1. The catalyst is then maintained for about 3 hours at about 400° C. in a stream of hydrogen before injecting the feed.

The isomerization process of the invention includes bringing at least one feed comprising at least one aromatic compound containing eight carbon atoms per molecule into contact with at least one catalyst having the composition described above and prepared using the process described above, said catalyst being present in a reactor in which the isomerization reaction occurs. Said feed comprising at least one aromatic compound containing eight carbon atoms per molecule comprises either solely a mixture of xylenes or solely ethylbenzene, or a mixture of xylenes and ethylbenzene. Said isomerization process of the invention is advantageously carried out using the following operating conditions:
- a temperature in the range 300° C. to 500° C., preferably in the range 320° C. to 450° C. and more preferably in the range 340° C. to 430° C.;
- a partial pressure of hydrogen in the range 0.3 to 1.5 MPa, preferably in the range 0.4 to 1.2 MPa and more preferably in the range 0.7 to 1.2 MPa;
- a total pressure in the range 0.45 to 1.9 MPa, preferably in the range 0.6 to 1.5 MPa; and
- a space velocity, expressed in kilograms of feed introduced per kilogram of catalyst per hour, in the range 0.25 to 30 $h^{-1}$, preferably in the range 1 to 10 $h^{-1}$ and more preferably in the range 2 to 6 $h^{-1}$.

The following examples illustrate the invention without in any way limiting its scope.

Example 1

Preparation of Catalyst a Comprising an EU-1 Zeolite Modified by CVD, Alumina and Platinum (in Accordance with the Invention)

The starting zeolite was an EU-1 zeolite with a Si/Al atomic ratio of 15, in the $H^+$ form. Passivation of the outer surface was carried out by gas phase deposition (CVD) with a layer of tetraethoxysilane (TEOS).

40 g of EU-1 zeolite was introduced into a fixed bed reactor where it initially underwent activation in a stream of nitrogen at 550° C. The temperature of the reactor was then reduced to 150° C., then a partial pressure of 0.15 bars of TEOS (Si(OCH$_2$CH$_3$)$_4$) was added to the nitrogen stream. After 2 h of reaction, the zeolite was stripped for 2 hours in nitrogen at 150° C. to evacuate the unreacted TEOS. The TEOS was decomposed in air at 450° C. for 3 hours.

Elemental analysis showed that the Si/Al atomic ratio (mol/mol) was 18: this increase in the Si/Al atomic ratio was explained by the deposition of 17% by weight with respect to the initial weight of the zeolite of a layer of amorphous silica on the outer surface of each crystal of the EU-1 zeolite.

The modified EU-1 was then formed by extrusion (extrusion diameter 1.4 mm) with an alumina gel to obtain, after drying and calcining in dry air, a support S1 which contained 10% by weight of EU-1 zeolite modified by CVD in the hydrogen form and 90% by weight of alumina.

Said support S1 underwent anion exchange with hexachloroplatinic acid in the presence of a competing agent (hydrochloric acid), to deposit on the alumina 1% by weight of platinum with respect to the catalyst weight. The wet solid was then dried at 120° C. for 12 hours and calcined in a stream of dry air at a temperature of 500° C. for one hour.

Catalyst A obtained contained, by weight, 10% of EU-1 zeolite modified by CVD, 89% of alumina and 1% of platinum.

Example 2

Preparation of Catalyst B Comprising an EU-1 Zeolite Modified by CLD, Alumina and Platinum (not in Accordance with the Invention)

The starting zeolite was an EU-1 zeolite with a Si/Al atomic ratio of 15, in the $H^+$ form. Passivation of the outer surface was carried out by liquid phase deposition (CLD) of a layer of tetraethoxysilane (TEOS).

40 g of EU-1 zeolite was introduced into a fixed bed reactor where it initially underwent activation in a stream of nitrogen at 550° C. The temperature of the reactor was then reduced to ambient temperature. The zeolite was then dissolved in anhydrous toluene (V/W=10). 50 g of TEOS, the quantity required to obtain a final material with a Si/Al (mol/mol) ratio of 18, was added to the anhydrous toluene under reflux. The solution was stirred for 2 hours. After reacting for 2 hours, the toluene was vacuum evaporated using a rotary evaporator. The TEOS was then decomposed in a fixed bed reactor, in air at 450° C. for 3 hours.

Elemental analysis showed that the Si/Al atomic ratio (mol/mol) was 18: this increase in the Si/Al atomic ratio is explained by the deposition of 17% by weight with respect to the initial weight of the zeolite of a layer of amorphous silica on the outer surface of each crystal of the EU-1 zeolite.

The modified EU-1 was then formed by extrusion (extrusion diameter 1.4 mm) with an alumina gel to obtain, after drying and calcining in dry air, a support S2 which contained 10% by weight of EU-1 zeolite modified by CLD in the hydrogen form, and 90% by weight of alumina.

Said support S2 underwent anion exchange with hexachloroplatinic acid in the presence of a competing agent (hydrochloric acid), to deposit on the alumina 1% by weight of platinum with respect to the catalyst weight. The wet solid was then dried at 120° C. for 12 hours and calcined in a stream of dry air at a temperature of 500° C. for one hour.

Catalyst B obtained contained, by weight, 10% of EU-1 zeolite modified by CLD, 89% of alumina and 1% of platinum.

Example 3

Evaluation of Catalytic Properties of Catalysts A and B in the Isomerization of Ethylbenzene The feed to be isomerized, brought into contact with catalyst A then with catalyst B, was constituted solely by ethylbenzene.

The operating conditions for the isomerization reaction were as follows:
- temperature: 385° C.;
- total pressure: 10 bars (1 bar=0.1 MPa);
- partial pressure of hydrogen: 8 bars;
- feed: ethylbenzene;
- space velocity, expressed in kilograms of feed introduced per kilogram of catalyst per hour, of 4 h$^{-1}$.

The catalytic properties of catalysts A and B were evaluated in succession for the isomerization of ethylbenzene. Each catalyst, A and B, was reduced in hydrogen for 4 hours at 480° C. before injecting the feed.

The catalysts were evaluated in terms of activity, which corresponded to the conversion of ethylbenzene.

The ethylbenzene conversion, denoted $CV_{EB}$, was equal to: 100-% by weight of ethylbenzene in the effluent. The percentage by weight of ethylbenzene in the effluent was obtained by chromatographic analysis of the effluent.

TABLE 1

Activity of catalysts A and B

|  | Catalyst A | Catalyst B |
|---|---|---|
| Ethylbenzene conversion (wt %) | 38 | 33 |

The results shown in Table 1 show that catalyst A comprising EU-1 zeolite surface modified by depositing a layer of amorphous silica via a gas phase treatment produced better catalytic performances as regards activity than those obtained using catalyst B comprising an EU-1 zeolite modified by a treatment step carried out in the presence of a molecular compound containing silicon in the liquid phase.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The preceding examples can be repeated with similar success by substituting the generically or specifically described reactants and/or operating conditions of this invention for those used in the preceding examples.

The entire disclosures of all applications, patents and publications, cited herein and of corresponding French application No. 06/10.979, filed Dec. 13, 2006 are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for isomerising a feed comprising at least one aromatic compound containing eight carbon atoms per molecule carried out in the presence of at least one catalyst comprising at least one modified zeolite with structure type EUO, at least one binder and at least one metal from group VIII of the periodic table, said catalyst having been prepared by a process which comprises at least the following steps in succession:
   a) a step for treatment of a zeolite with structure type EUO in the presence of at least one molecular compound containing at least one silicon atom, during which said compound, with a diameter greater than the maximum pore opening diameter in said zeolite, is deposited in the gas phase in the absence of any hydrocarbon compound on the outer surface of said zeolite;
   b) at least one heat treatment step sufficient to decompose said molecular compound in step a) to amorphous silica on the outer surface of said zeolite to form a modified zeolite;
   c) a step for forming said modified zeolite with a binder;
   d) at least one step for introducing at least one metal from group VIII of the periodic table onto a support comprising resultant modified and formed zeolite.

2. An isomerization process according to claim 1, in which said group VIII metal included in said catalyst is platinum.

3. An isomerization process according to claim 1, in which said catalyst comprises at least one additional metal selected from the group formed by elements from groups IIIA, IVA and VIIB.

4. An isomerization process according to claim 3, in which said additional metal is selected from indium, tin and rhenium.

5. An isomerization process according to claim 1, in which said catalyst is in the form of extrudates.

6. An isomerization process according to claim 1, in which before being modified in said step a), said zeolite with structure type EUO contains at least silicon and aluminium in a proportion such that the atomic ratio Si/Al is in the range 2:1 to 100:1.

7. An isomerization process according to claim 1, in which said zeolite with structure type EUO is EU-1 zeolite.

8. An isomerization process according to claim 1, in which said molecular compound containing at least one silicon atom used in said step a) is selected from compounds with formula Si—R$_4$ and Si$_2$—R$_6$, where R may either be hydrogen, an alkyl, aryl or acyl group, an alkoxy group (O—R'), a hydroxyl group (—OH) or a halogen, R being identical or different.

9. An isomerization process according to claim 1, in which said molecular compound employed in said step a) has a composition with general formula Si—(OR')$_4$, where R' is an alkyl, aryl or acyl group.

10. An isomerization process according to claim 1, in which said step a) is carried out in a fixed bed reactor.

11. An isomerization process according to claim 1, in which the heat treatment of said step b) is carried out at a temperature in the range 200° C. to 700° C.

12. An isomerization process according to claim 1, which is carried out under the following operating conditions: a temperature in the range 300° C. to 500° C., a partial pressure of hydrogen in the range 0.3 to 1.5 MPa, a total pressure in the range 0.45 to 1.9 MPa, and a space velocity, expressed in kilograms of feed introduced per kilogram of catalyst per hour, in the range 0.25 to 30 h$^{-1}$.

13. An isomerization process according to claim 1, wherein the aromatic compound is ethyl benzene, the zeolite with structural type EUO is EU-1 zeolite, the molecular compound of step a) is tetraethoxysilane, the heat treatment of step b) is conducted at 200°-700° C., the binder is alumina, and the group VIII metal is platinum.

14. An isomerization process according to claim 12, wherein the aromatic compound is ethyl benzene, the zeolite with structural type EUO is EU-1 zeolite, the molecular compound of step a) is tetraethoxysilane, the heat treatment of step b) is conducted at 200°-700° C., the binder is alumina, and the group VIII metal is platinum.

15. A process according to claim 1, wherein after step (b) there are no further steps for adding molecules containing silicon to the surface of the zeolite.

16. A process according to claim 13, wherein after step (b) there are no further steps for adding molecules containing silicon to the surface of the zeolite.

17. An isomerization process according to claim 15, in which said molecular compound employed in said step a) has a composition with general formula $Si-(OR')_4$, where R' is an alkyl, aryl or acyl group.

* * * * *